United States Patent
Govari et al.

(10) Patent No.: US 11,918,298 B2
(45) Date of Patent: Mar. 5, 2024

(54) VERY NARROW PROBE WITH COIL

(71) Applicant: Biosense Webster (Israel) Ltd., Yokneam (IL)

(72) Inventors: Assaf Govari, Haifa (IL); Christopher Thomas Beeckler, Brea, CA (US); Vadim Gliner, Haifa (IL); Joseph Thomas Keyes, Glendora, CA (US); Athanassios Papaioannou, Los Angeles, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 313 days.

(21) Appl. No.: 16/568,415

(22) Filed: Sep. 12, 2019

(65) Prior Publication Data
US 2021/0077197 A1    Mar. 18, 2021

(51) Int. Cl.
| A61B 34/20 | (2016.01) |
| A61B 5/06 | (2006.01) |
| A61B 18/14 | (2006.01) |
| A61B 90/00 | (2016.01) |
| G01B 7/004 | (2006.01) |

(52) U.S. Cl.
CPC .............. *A61B 34/20* (2016.02); *A61B 5/062* (2013.01); *A61B 18/1492* (2013.01); *A61B 90/36* (2016.02); *G01B 7/004* (2013.01); *A61B 2018/1435* (2013.01); *A61B 2034/2051* (2016.02); *A61B 2090/3925* (2016.02); *A61B 2090/397* (2016.02); *A61B 2562/0223* (2013.01); *A61B 2562/16* (2013.01)

(58) Field of Classification Search
CPC ......... A61B 34/20; A61B 90/36; A61B 5/062; A61B 18/1492; A61B 2034/2051; A61B 2090/3925; A61B 2018/1435; A61B 2562/0223; A61B 2562/16; G01B 7/004; H01F 27/255; H01F 1/37
See application file for complete search history.

(56) References Cited

U.S. PATENT DOCUMENTS

| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |

(Continued)

FOREIGN PATENT DOCUMENTS

| DE | 102017217990 A1 * | 4/2019 |
| EP | 3106195 A2 | 12/2016 |

(Continued)

OTHER PUBLICATIONS

Machine translation of DE102017217990A1 (Year: 2019).*

(Continued)

*Primary Examiner* — John D Li
(74) *Attorney, Agent, or Firm* — Troutman Pepper Hamilton Sanders LLP (57) ABSTRACT

In one embodiment, a probe apparatus includes a shaft having a distal end, a tube containing separate powder granules of a ferrite, the tube being fixed to the distal end of the shaft, a coil disposed around the tube, and electrical wires connected to the coil so as to read out a signal generated across the coil due to an externally-applied magnetic field.

16 Claims, 7 Drawing Sheets

(56) References Cited

U.S. PATENT DOCUMENTS

| | | | |
|---|---|---|---|
| 6,690,963 B2 | 2/2004 | Ben-Haim et al. | |
| 7,756,576 B2 | 7/2010 | Levin | |
| 7,848,787 B2 | 12/2010 | Osadchy | |
| 7,869,865 B2 | 1/2011 | Govari et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2006/0271135 A1* | 11/2006 | Minar | A61L 29/085 607/116 |
| 2009/0005757 A1* | 1/2009 | Taber | A61M 25/01 604/523 |
| 2011/0066029 A1 | 3/2011 | Lyu et al. | |
| 2012/0172842 A1* | 7/2012 | Sela | B29C 63/18 604/528 |
| 2014/0371709 A1 | 12/2014 | Allen et al. | |
| 2015/0359549 A1* | 12/2015 | Lenker | A61B 17/12118 600/585 |
| 2016/0022154 A1 | 1/2016 | Warnking et al. | |
| 2016/0095733 A1* | 4/2016 | Sharma | A61F 2/04 600/424 |
| 2016/0372252 A1* | 12/2016 | Gliner | A61B 34/20 |
| 2017/0209099 A1* | 7/2017 | Caron | A61B 5/02158 |
| 2017/0360283 A1* | 12/2017 | Kimura | H02J 50/10 |
| 2018/0015261 A1* | 1/2018 | Lippert | A61L 31/18 |
| 2019/0009060 A1* | 1/2019 | Eboli | A61M 25/0662 |
| 2019/0022363 A1 | 1/2019 | Grayzel et al. | |
| 2019/0175282 A1* | 6/2019 | Akbarian | A61B 17/32002 |
| 2019/0357984 A1 | 11/2019 | Govari | |

FOREIGN PATENT DOCUMENTS

| | | | | |
|---|---|---|---|---|
| JP | 2001135516 A | * | 5/2001 | H01F 1/083 |
| WO | 1996005768 A1 | | 2/1996 | |
| WO | 9729682 A1 | | 8/1997 | |
| WO | 2017210020 A1 | | 12/2017 | |

OTHER PUBLICATIONS

Machine Translation of JP2001135516A (Year: 2023).*
EP 20195722.2-1122 Extended European Search Report dated Nov. 2, 2020.
U.S. Appl. No. 15/674,380, filed Aug. 10, 2017, entitled "ENT Image Registration".

* cited by examiner

VERY NARROW PROBE WITH COIL

FIELD OF THE INVENTION

The present invention relates to medical equipment, and in particular, but not exclusively to, probes with navigational features.

BACKGROUND

A wide range of medical procedures involve placing probes, such as guidewires and catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2003/0120150 and 2004/0068178, whose disclosures are all incorporated herein by reference.

Navigable guidewires typically have diameters of the order of 1 mm or more, and this limits parts of the body that they are able to enter, for instance extremities of the lungs and some blood vessels in the brain.

US Patent Publication 2016/0022154 of Warnking, et al., describes a system for detection of blood pressure in a blood vessel including a guidewire and an LC resonance circuit provided at a distal end of the guidewire. The resonance circuit may be a non-LC resonance circuit responsive to changes in pressure of fluid external to the guidewire such that the resonance circuit has a resonance frequency that varies in accordance with changes in pressure of the external fluid.

US Patent Publication 2014/0371709 of Allen, et al., describes a catheter assembly with a catheter body and an inflatable balloon. The catheter body has a proximal end, a distal end and a balloon inflation lumen. The inflatable balloon is attachable to the distal end of the catheter body. The balloon has an inner surface that at least partially defines an interior volume. The balloon is configured such that the interior volume can be in fluid communication with the inflation lumen of the catheter body to inflate the balloon. The balloon also has a proximal surface and a distal surface. The balloon is provided with a channel that extends through the balloon. The channel is configured to provide fluid communication between the proximal surface of the balloon and the distal surface of the balloon. Other catheter assemblies and methods of use are also disclosed.

US Patent Publication 2019/0022363 of Grayzel, et al., describes medical guide elements for use with dilators to be inserted into an organ or body structure of a patient, such as the kidney. The guide element includes a proximal segment and a distal segment. The diameter of the distal segment is greater than the diameter of the proximal segment. The change in diameter is abrupt, providing a discrete step transition at a point along the filament which presents a proximally-facing surface on the distal segment. When the proximal segment of the guide element is fully inserted into a dilator having a distal tip adapted for insertion into a patient, the dilator distal tip firmly abuts the proximally-facing end surface of the distal segment. The relative dimensions of the dilator tip and the discrete stepped transition of the guide element provides full shielding or over shielding of the dilator tip, thereby facilitating passage of the dilator tip along the tissue track, through the puncture hole and into the orifice.

SUMMARY

There is provided in accordance with an embodiment of the present disclosure, a probe apparatus, including a shaft having a distal end, a tube containing separate powder granules of a ferrite, the tube being fixed to the distal end of the shaft, a coil disposed around the tube, and electrical wires connected to the coil so as to read out a signal generated across the coil due to an externally-applied magnetic field.

Further in accordance with an embodiment of the present disclosure the tube has an inner diameter of less than 150 microns.

Still further in accordance with an embodiment of the present disclosure, the apparatus includes a guidewire including a solid rod core wire including a distal end and a surface channel for accepting the electrical wires therein, a shapeable elongated member, connected to the distal end of the core wire, and configured to retain a shape after being deformed, and a resilient elongated member disposed around the shapeable elongated member, wherein the tube is disposed distally to the resilient elongated member and the shapeable elongated member.

Additionally, in accordance with an embodiment of the present disclosure the surface channel spirals around the core wire away from the distal end of the core wire.

Moreover, in accordance with an embodiment of the present disclosure the shapeable elongated member includes a flat wire helical spring.

Further in accordance with an embodiment of the present disclosure the resilient elongated member includes an outside surface including a plurality of cut grooves disposed around the outside surface.

Still further in accordance with an embodiment of the present disclosure the guidewire includes a shrink sleeve disposed over the core wire retaining the electrical wires in the surface channel.

Additionally, in accordance with an embodiment of the present disclosure the tube is formed from plastic.

Moreover, in accordance with an embodiment of the present disclosure the plastic includes polyimide.

There is also provided in accordance with another embodiment of the present disclosure, a position tracking system, including a probe configured to be inserted into a body part of a living subject, and including a shaft having a distal end, a tube containing separate powder granules of a ferrite, the tube being fixed to the distal end of the shaft, a coil disposed around the tube, and electrical wires connected to the coil so as to read out a signal generated across the coil due to an applied magnetic field, a location pad having at least one magnetic field radiator configured to transmit alternating magnetic fields into a region where the body part is located, and processing circuitry coupled to the electrical wires, and configured to receive the signal from the coil, and compute a position and orientation of the distal end responsively to the received signal.

Further in accordance with an embodiment of the present disclosure the tube has an inner diameter of less than 150 microns.

Still further in accordance with an embodiment of the present disclosure the probe includes a guidewire including a solid rod core wire including a distal end and a surface channel for accepting the electrical wires therein, a shapeable elongated member, connected to the distal end of the core wire, and configured to retain a shape after being deformed, and a resilient elongated member disposed around the shapeable elongated member, wherein the tube is disposed distally to the resilient elongated member and the shapeable elongated member.

Additionally, in accordance with an embodiment of the present disclosure the tube is formed from plastic.

Moreover, in accordance with an embodiment of the present disclosure the plastic includes polyimide.

There is also provided in accordance with still another embodiment of the present disclosure, a method to produce a magnetic coil, including introducing separate powder granules of a ferrite into a tube, and disposing a coil around the tube.

Further in accordance with an embodiment of the present disclosure the tube has an inner diameter of less than 150 microns.

Still further in accordance with an embodiment of the present disclosure while the powder granules are introduced into the tube, the tube has an outer diameter which is greater than an inner diameter of the coil, the method further including heat shrinking the tube to have an outer diameter less than the inner diameter of the coil.

Additionally, in accordance with an embodiment of the present disclosure, the method includes suspending the powder granules in a liquid, disposing the tube in the liquid so that capillary action draws some of the liquid with the powder granules into the tube, and causing evaporation of the liquid from the tube.

Moreover, in accordance with an embodiment of the present disclosure the liquid is an alcohol.

Further in accordance with an embodiment of the present disclosure the tube is formed from plastic.

Still further in accordance with an embodiment of the present disclosure the plastic includes polyimide.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

As previously mentioned, navigable probes such as guidewires typically have diameters of the order of 1 mm or more, and this limits parts of the body that they are able to enter, for instance extremities of the lungs and some blood vessels in the brain.

Making a probe of a smaller diameter, equal to or less than 0.9 mm, such as about 300 microns or less, is not just a simple miniaturization task by making the various elements of the probe smaller. One such challenge is producing a small enough magnetic core for a navigation coil of the probe.

For example, magnetic antennas can use a magnetic core made of a ferromagnetic or ferrimagnetic material such as iron or a nickel-zinc ferrite or magnesium-zinc ferrite to increase permeability. A magnetic core can increase the sensitivity of an antenna by a factor of up to several thousand, by increasing the magnetic field due to its higher magnetic permeability. Therefore, coils used in navigable probes typically include coils with a magnetic core. A solid magnetic core may be constructed by any suitable method including joining magnetic-core powder using a binder and/or very high temperatures (sintering) to form a solid mass. However, the above production methods are generally not suitable for producing solid magnetic cores which are small enough to insert into a coil having an inner diameter of about 500 microns or less.

Embodiments of the present invention provide a probe including a shaft having a distal end, and a tube fixed to the distal end of the shaft. The tube contains separate powder granules of a ferrite and a coil is placed around the tube, for example, by inserting the tube into the coil. The coil is in turn covered with a covering keeping the coil in place and acting as a biocompatible cover. The wire used in the coil may have any suitable gauge, for example, but not limited to 60 gauge which is about 8 microns in diameter. The powder granules are held in place by the tube. The powder granules are not sintered to form a single mass but they may be bound together using a binder material such as epoxy. The tube may be formed from any suitable material such as a wide-range of thermoplastics, e.g., polyimide, polyamide, polyethylene terephthalate (PET), fluorinated ethylene propylene (FEP), or polyvinyl chloride (PVC) or other materials such as an engineered ceramic, a carbon material, or a non-ferromagnetic metal. The tube provides a controlled outer diameter surface on which to slide the coil.

Electrical wires connect to the coil so as to read out a signal generated across the coil due to an externally-applied magnetic field. The signals provided by the coil are used to compute a position and orientation of the distal end of the probe. The powder granules increase the magnetic permeability of the coil and increase the amplitude of the signals provided by the coil.

As the powder granules may have a size of about 40 microns, it is difficult to place the powder granules into the tube, which in some embodiments may have an inner diameter of down to 100. In some cases, the powder granules have a size which is about the radius of the tube. The present invention, in embodiments thereof, provides novel methods for introducing the powder granules into the tube.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

In some embodiments, the powder granules are placed in a heat-shrinkable tube which has an outer diameter which is greater than the inner diameter of the coil. For example, the powder granules maybe placed in a tube having an inner diameter of about 180 microns and an outer diameter of about 250 microns. It is significantly easier to place the powder granules in a tube with an inner diameter of about 180 microns than it is to place the powder granules in a tube with an inner diameter of 150 microns or less. Heat is then applied to the tube to heat-shrink it until the outer diameter is equal to the inner diameter of the coil. The heat-shrunk tube is then inserted into the coil. The tube may be formed from any suitable material, such as a wide-range of thermoplastics, e.g., polyimide, polyamide, polyethylene terephthalate (PET), fluorinated ethylene propylene (FEP), or polyvinyl chloride (PVC).

In some embodiments, the powder granules are suspended in a liquid such as an alcohol, e.g., isopropyl alcohol, using a vibration table, for example. An end of a tube, which has an outer diameter less than the inner diameter of the coil, is then placed in the liquid and through capillary action the powder granule suspension is drawn into the tube. An evaporation process is then initiated to evaporate the liquid in the tube, leaving the powder granules in the tube. The powder-granule-filled tube is inserted into the coil. The tube may be formed from any suitable material, such as a wide-range of thermoplastics, e.g., polyimide, polyamide, polyethylene terephthalate (PET), fluorinated ethylene propylene (FEP), or polyvinyl chloride (PVC).

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1A:
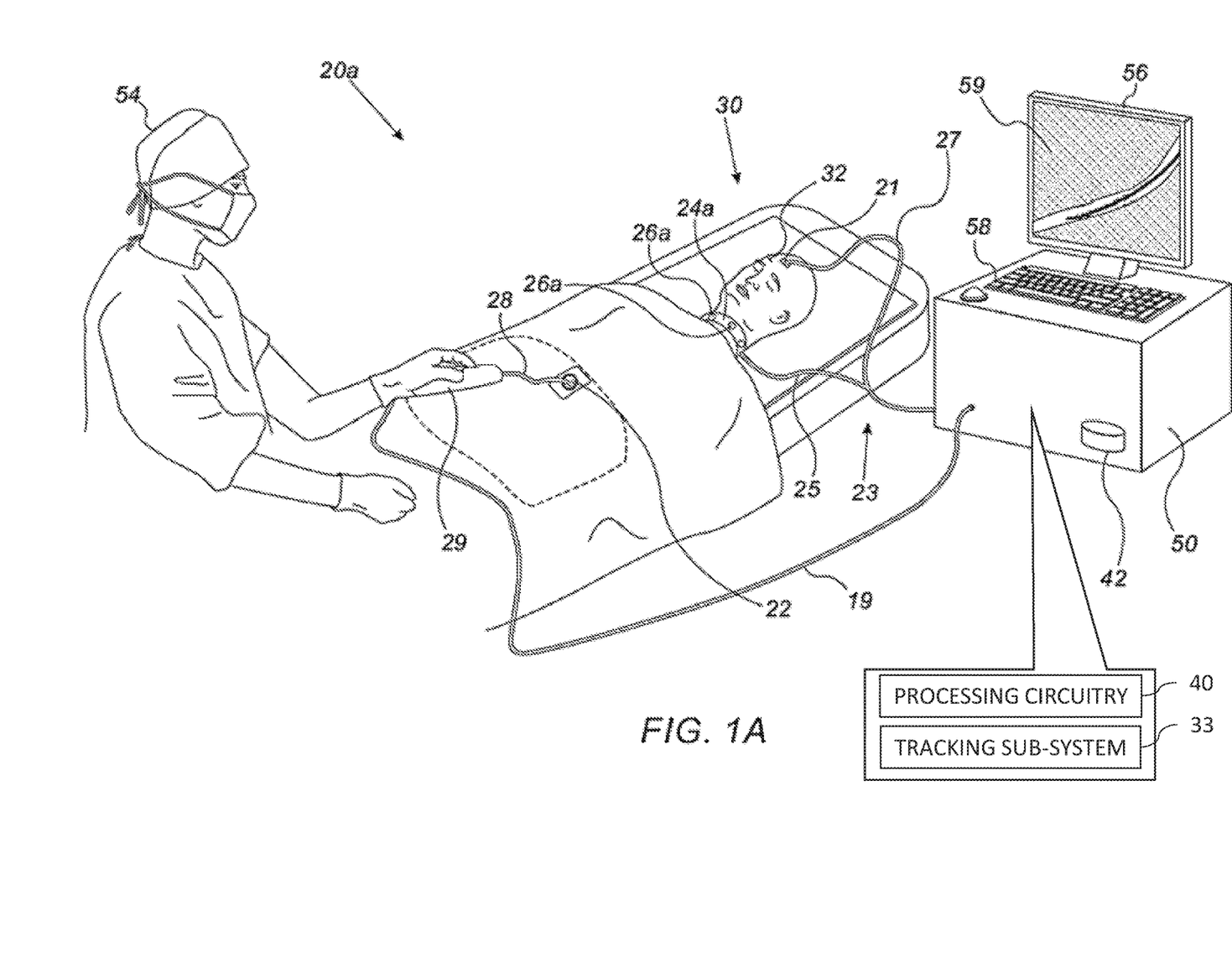
FIGS. 1A and 1B are schematic, pictorial illustrations of probe-based cerebrovascular position tracking systems, in accordance with embodiments of the present invention.
Figure 1B:
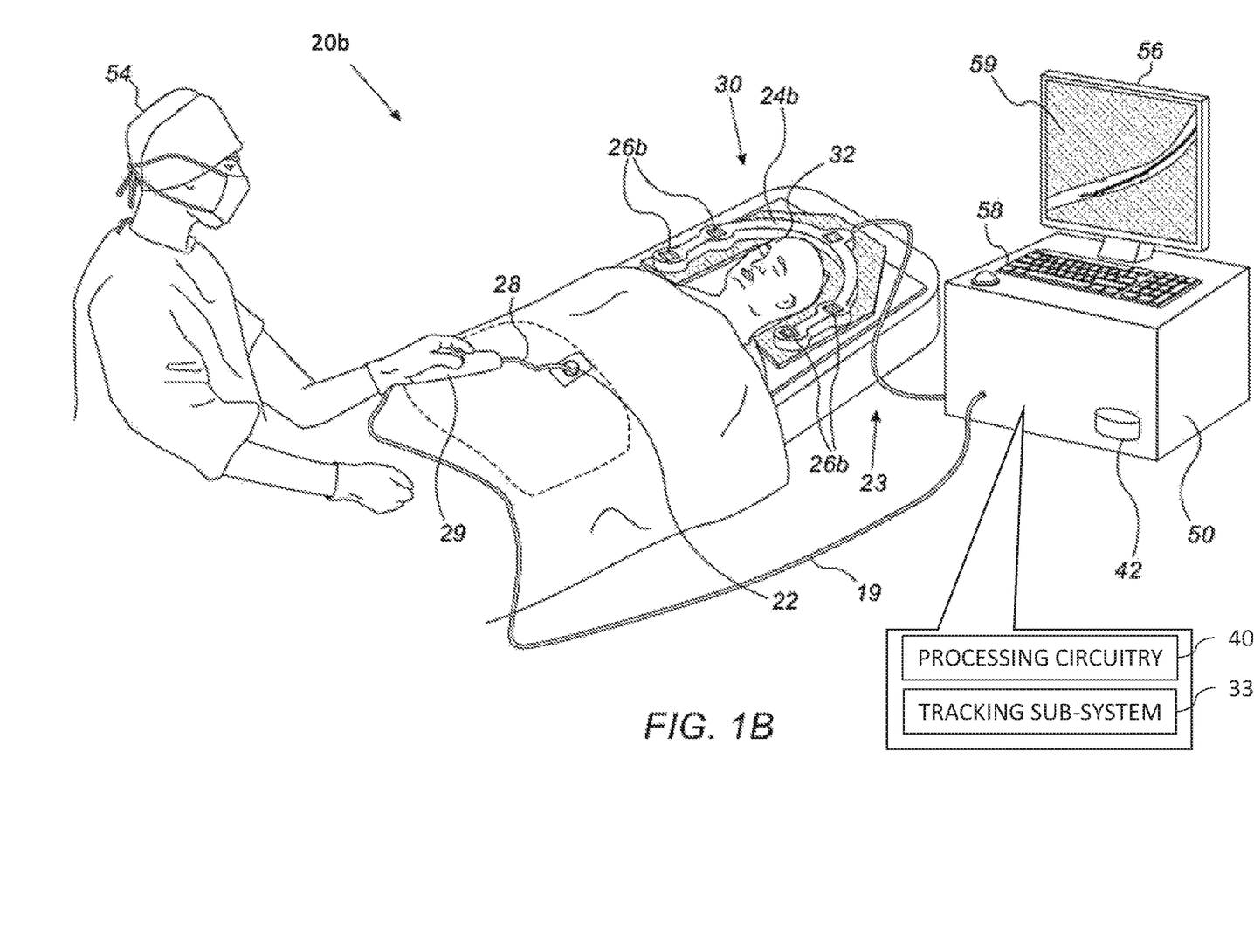

FIGS. 1A and 1B are schematic, pictorial illustrations of probe-based cerebrovascular position tracking systems 20a and 20b, in accordance with embodiments of the present invention.

In some embodiments, prior to performing a medical procedure, CT images of a patient 32 are acquired. The CT images are stored in a memory 42 for subsequent retrieval by processing circuitry 40. The processing circuitry 40 uses the images to present, for example, a brain section image 59 on a display 56. In another embodiment, during the disclosed medical procedure, tracking systems 20a and 20b register a position and orientation of a distal end of a probe 28 inside the patient's brain, with frames of reference of brain images of the patient 32, herein assumed by way of example to comprise real-time fluoroscopic images. The position and orientation of the distal end of the probe 28 is tracked using a magnetic tracking subsystem 23, which tracks position and orientation coordinates of a magnetic sensor fitted at the distal end of the probe 28. The magnetic tracking subsystem 23 may form part of a tracking subsystem 33. Using magnetic position and orientation tracking subsystem 23, a physician 54 advances the distal end of the probe 28 through vasculature.

In system 20a, shown in FIG. 1A, a location pad 24a, comprised in magnetic tracking subsystem 23, is implemented as a collar around the neck of patient 32. By putting location pad 24a around the neck, location pad 24a is configured to automatically compensate for patient head movement. Location pad 24a comprises magnetic field radiators 26a which are fixed in position relative to the head of patient 32 and which transmit alternating sinusoidal magnetic fields into a region 30 where the head of patient 32 is located. A console 50 electrically drives radiators 26a via a cable 25. In an embodiment, further compensation of head motion is provided by attaching a reference sensor 21 to the patient's forehead. Console 50 is configured to receive signals from reference sensor 21 via a cable 27. A location tracking system that comprises a neck collar location pad is described in U.S. patent application Ser. No. 16/248,393, filed Jan. 15, 2019, entitled "Position Sensor on Brain Clot Sheath and Location Pad Collar," which is assigned to the assignee of the present patent application and whose disclosure is incorporated herein by reference.

Physician 54, operating system 20a, holds a controller handle 29, which is connected to the proximal end of probe 28. Controller handle 29 allows the physician to advance and navigate probe 28 in the brain, for example, through an entry point 22 at an artery at a thigh of patient 32. As noted above and described below, physician 54 navigates the distal end of probe 28 using position and orientation signals from a magnetic sensor fitted at the distal end of probe 28. Console 50 receives the magnetic sensor signals via a cable 19 that connects to probe 28 via handle 29.

Elements of system 20a, including radiators 26a, are controlled by processing circuitry 40, comprising a processing unit communicating with one or more memories (e.g., the memory 42). Processing circuitry 40 may be mounted in console 50, which comprises operating controls 58 that typically include a keypad and/or a pointing device such as a mouse or trackball. Physician 54 may use operating controls on handle 29 to interact with the processing circuitry 40 while performing the registration of system 20a. During the registration process, an image 59 of a brain section is presented on display 56. Subsequent to the registration process described above, physician 54 uses the operating controls to advance the distal end of probe 28 to one or more desired locations in the brain.

Processing circuitry 40 uses software stored in the memory 42 to operate system 20a. In practice, some or all of the functions of the processing circuitry 40 may be combined in a single physical component or, alternatively, implemented using multiple physical components. These physical components may comprise hard-wired or programmable devices, or a combination of the two. In some embodiments, at least some of the functions of the processing circuitry 40 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

System 20b, shown in FIG. 1B, has a different magnetic location pad design, namely a location pad 24b. As seen, location pad 24b is fixed to the bed, and irradiators 26b surround a patient headrest horizontally. In this example, system 20b lacks reference sensor 21, and therefore the head of the patient must be harnessed to prevent motion of the head. Other components of system 20b are generally identical to those of system 20a. A location tracking system using a location pad similar to location pad 24b is described in U.S. patent application Ser. No. 15/674,380, filed Aug. 10, 2017, entitled "ENT Image Registration," which is assigned to the assignee of the present patent application and whose disclosure is incorporated herein by reference.

Systems 20a and 20b shown in FIGS. 1A and 1B are chosen purely for the sake of conceptual clarity. Other system elements may be included, for example additional controls on handle 29 for controlling additional tooling such as for drug delivery.

Carto® magnetic tracking systems, which track a location and orientation of a magnetic position sensor in an organ of a body using techniques similar to those applied by systems 20a and 20b, are produced by Biosense-Webster (Irvine, California). In general, position sensing using current distribution measurements and/or external magnetic fields are described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1, whose disclosures are all incorporated herein by reference.

The above description describes navigating a probe in blood vessels of the brain. The system 20a and 20b may be suitably adapted to navigate a probe in a suitable body part within a living subject, for example, sinus cavities, a heart or a kidney. The probe 28 may be implemented as any suitable probe with a magnetic coil for navigation purposes. The probe may include a guidewire and/or a catheter by way of example only. If the probe 28 is implemented as a guidewire, the guidewire may be used to being a catheter into the living subject on top of the guidewire once the guidewire is located correctly. For example, in some cases a catheter may be too bulky and/or floppy to insert into a living subject on its own without first using a guidewire.

Figure 2:
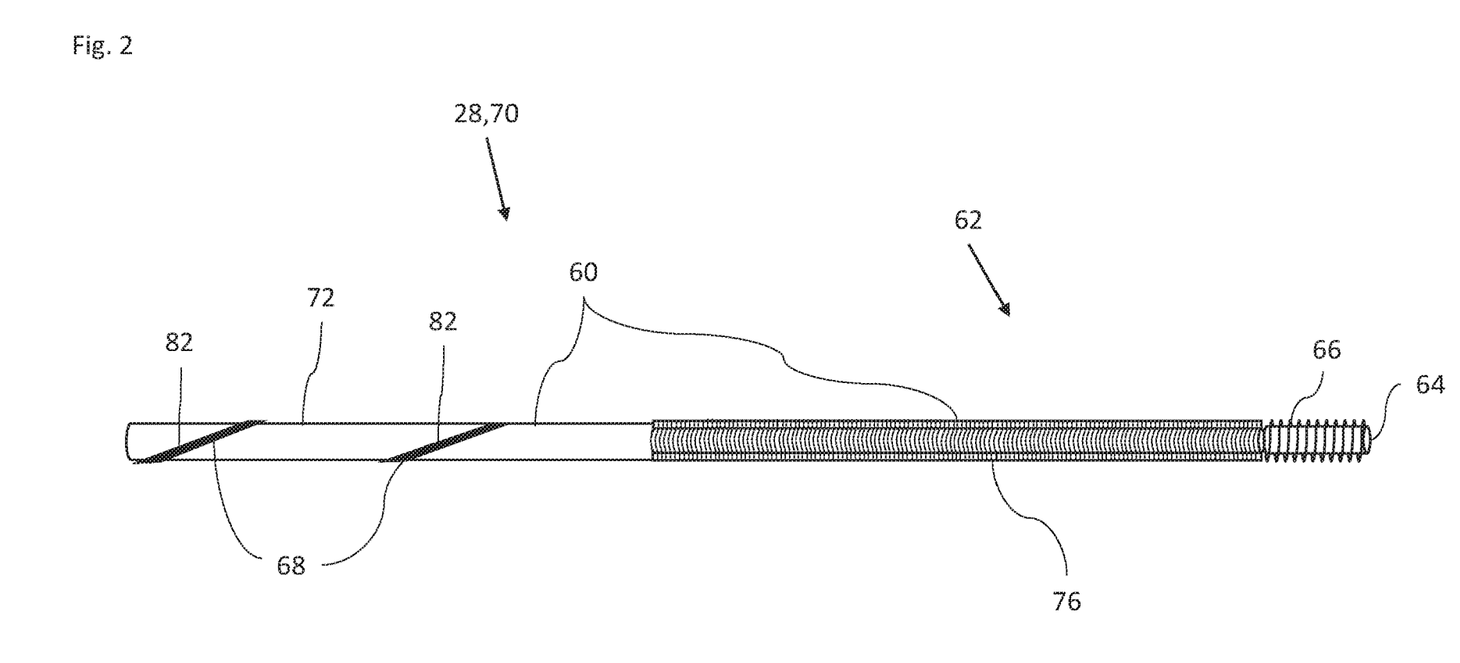
FIG. 2 is a schematic view of a probe for use in the systems of FIG. 1A or 1B.
Figure 3:
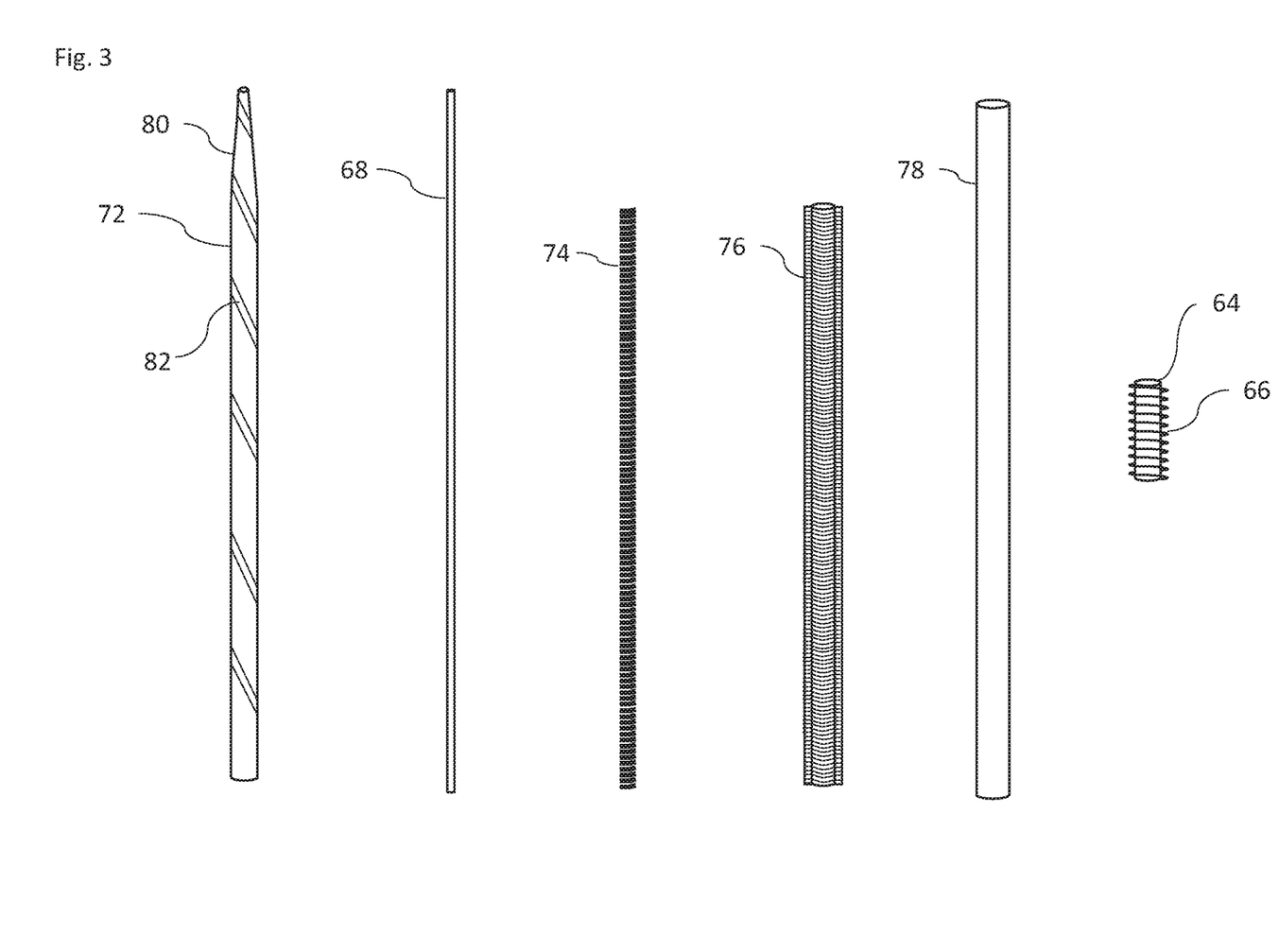
FIG. 3 is a schematic view of elements of the probe of FIG. 2.

Reference is now made to FIGS. 2 and 3. FIG. 2 is a schematic view of the probe 28 for use in the systems 20a and 20b of FIG. 1A or 1B. FIG. 3 is a schematic view of elements of the probe 28 of FIG. 2.

The probe 28 described with reference to FIGS. 2 and 3 includes a guidewire comprising various elements. In some embodiments, the probe 28 may be implemented with different elements than those described below, while still providing a deflectable probe with an integrated magnetic coil for navigation purposes. In some embodiments, the probe 28 may be any suitable probe, such as a catheter or an ENT tool, with an integrated magnetic coil for navigation purposes.

The probe 28 is configured to be inserted into any suitable body part of a living subject. The probe 28 includes a shaft 60 having a distal end 62.

The probe 28 includes a tube 64 containing separate powder granules of a ferrite. The tube 64 may have any suitable inner diameter. The inner diameter of the tube 64 is generally less than 150 microns and typically in the range of 100 to 750 microns. The tube 64 may have any suitable outer diameter, for example, but not limited to, less than 170 microns. The tube is formed from any suitable plastic or other suitable material which is thin enough and strong enough for the purpose, for example, but not limited to, polyimide. The tube 64 may be made of any suitable material, for example, but not limited to, a wide-range of thermoplastics, e.g., polyamide, polyethylene terephthalate (PET), fluorinated ethylene propylene (FEP), or polyvinyl chloride (PVC). The powder granules are not sintered bound together to form a single solid mass, but in some embodiments may be held together with a binding agent such as epoxy. The tube 64 is fixed to the distal end 62 of the shaft 60. The tube 64 and the powder granules are described in more detail with reference to FIGS. 4 and 5.

The probe 28 includes a coil 66 which is disposed around the tube 64. The coil 66 may include any suitable insulated wire. In some embodiments, the coil 66 is wound from insulated copper wire. The gauge of the wire may be any suitable gauge. In some embodiments, the wire is 60-gauge insulated copper wire, which has an outer diameter of about 8 microns. The coil is covered with any suitable cover (not shown), for example, but not limited to a plastic cover such as a plastic tube, or with a coating such an as enamel or epoxy paint, shrink sleeve, or metal cover. A metal cover may also provide shielding from high frequency electromagnetic interference.

The probe 28 includes electrical wires 68 connected to the coil 66 so as to read out a signal generated across the coil 66 due to an externally-applied magnetic field. In FIG. 2, the electrical wires 68 are shown spiraling down the shaft 60. The electrical wires 68 may be twisted pair conductors. The electrical wires 68 may be disposed in a cable. The conductors of the electrical wires 68 may comprise any suitable conductor, for example but not limited to, a copper alloy with 3% silver. The electrical wires 68 connect the coil 66 with a proximal end of the probe 28, described in more detail below.

The externally-applied magnetic field may be applied by the location pad 24a or 24b (FIGS. 1a and 1b, respectively) having at least one magnetic field radiator 26a or 26b (FIGS. 1a and 1b, respectively) configured to transmit alternating magnetic fields into a region where the body part is located.

The processing circuitry 40 (FIGS. 1a and 1b) is coupled to the electrical wires 68 via the cable 19 (FIGS. 1a and 1b). The processing circuitry 40 is configured to receive the signal from the coil 66 and compute a position and orientation of the distal end 62 responsively to the received signal.

Additional elements of the probe 28 are now described. FIG. 2 shows the probe 28 in its assembled form, whereas FIG. 3 shows the elements of the probe prior to assembly. The probe 28 includes a guidewire 70 comprising: a solid rod core-wire 72, the electrical wires 68 disposed in a single cable, a shapeable elongated member 74 (FIG. 3), a resilient elongated member 76, a shrink-sleeve 78 (FIG. 3); and the coil 66 around the tube 64.

The solid rod core-wire 72 includes a distal end 80 and a surface channel 82 cut into the solid rod core-wire 72 for accepting the electrical wires 68 therein (as shown in FIG. 2). In some embodiments, the surface channel 82 spirals around the core wire away from the distal end 80 of the core wire 72 towards the proximal end of the probe 28. The solid rod core-wire 72 may be formed from any suitable material for example, but not limited to, stainless steel, cobalt chromium or nitinol. The solid rod core-wire 72 may have any suitable length. In some embodiments, the solid rod core-wire 72 has a length in the range of 1-3 meters, for example about 2 meters. The solid rod core-wire 72 may have any suitable outer diameter. In some embodiments the solid rod core-wire 72 may have an outer diameter in the range of 200-900 microns, for example, 300 microns. The distal end 80 of the solid rod core-wire 72 may be tapered (as shown in FIG. 3), for example, by grinding the distal end 80. The tapered portion of the solid rod core-wire 72 may be used to accept the proximal end of the resilient elongated member 76 thereon.

The proximal end of the resilient elongated member 76 is disposed over, and connected to, the tapered distal end 80 of the solid rod core-wire 72. The shapeable elongated member 74 is disposed in the resilient elongated member 76 so that the resilient elongated member 76 is disposed around the shapeable elongated member 74. The tube 64 is disposed distally to the resilient elongated member 76 and the shapeable elongated member 74. The tube 64 is connected to the resilient elongated member 76 at the distal end of the resilient elongated member 76. The resilient elongated member 76 comprises an outside surface including a plurality of laser or mechanically cut grooves (or cut using any suitable method) disposed around the outside surface. The grooves make the resilient elongated member 76 more flexible. The resilient elongated member 76 may be formed from any suitable material. In some embodiments, the resilient elongated member 76 is formed from nitinol. The resilient elongated member 76 may have any suitable length. In some embodiments, the resilient elongated member 76 has a length in the range of 1-30 cm, for example about 15 cm. The resilient elongated member 76 may have any suitable outer width. In some embodiments the resilient elongated member 76 may have an outer width in the range of 275-900 microns, for example, 325 microns. The elongated member 76 may have any suitable inner diameter, for example, in the range of 150-800 microns, such as, 200 microns, and big enough to accommodate the shapeable elongated member 74 therein.

The shapeable elongated member 74 is connected to the distal end 80 of the core wire 72. The shapeable elongated member 74 is configured to retain a shape after being deformed by a physician who may intentionally deform the distal end of the probe 28 in order to navigate the probe 28 in one or more body parts. In some embodiments, the shapeable elongated member 74 includes a flat wire helical spring. The shapeable elongated member 74 may be formed of any suitable material. In some embodiments the shapeable elongated member 74 may be formed from stainless steel. The shapeable elongated member 74 may be any suitable length. In some embodiments, the shapeable elongated member 74 has a length in the range of 1-30 cm, for example, about 15 cm. The shapeable elongated member 74 is sized to fit inside the hollow of the resilient elongated member 76. In some embodiments, the shapeable elongated member 74 has an outer diameter in the range of 100 to 750 micros.

The electrical wires 68 which extend from the coil 66 are disposed through the center of the shapeable elongated member 74 and then around the surface channel 82 of the solid rod core-wire 72 until reaching the proximal end of the probe 28.

The shrink-sleeve 78 is disposed over the solid rod core-wire 72. The shrink-sleeve 78 helps retain the electrical wires 68 in the surface channel 82. The shrink-sleeve 78 may be formed from any suitable material, for example, a polyethylene terephthalate (PET) or a fluoropolymer. The shrink-sleeve 78 typically covers the solid rod core-wire 72 for its entire length. In some embodiments, the shrink-sleeve 78 may only partially cover the solid rod core-wire 72. In some embodiments the shrink sleeve 78 may also cover the resilient elongated member 76. For the sake of simplicity, the shrink-sleeve 78 is not shown in FIG. 2.

Figure 4A:
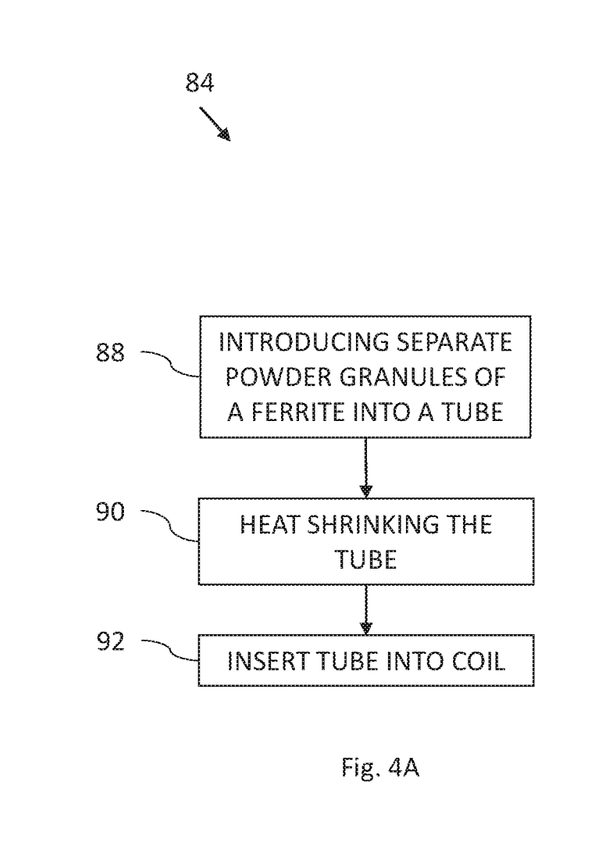
FIG. 4A is a flowchart including steps in a method of manufacture of a magnetic coil for use in the systems of FIG. 1A or 1B.
Figure 4B:
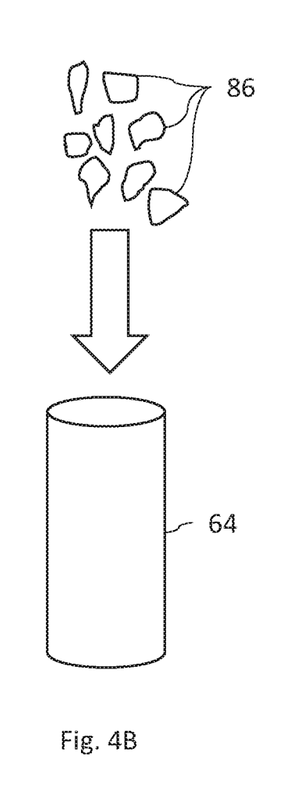
FIGS. 4B-4D are schematic views illustrating the method of manufacture described with reference to the flowchart of FIG. 4A.
Figure 4C:
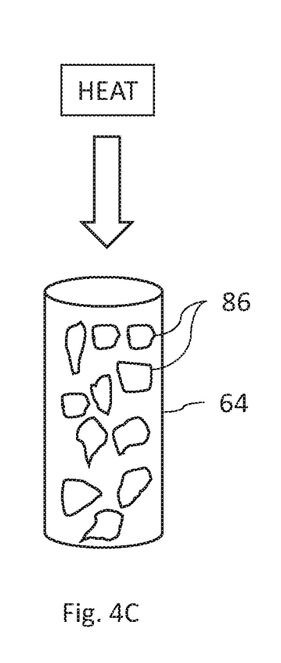
Figure 4D:
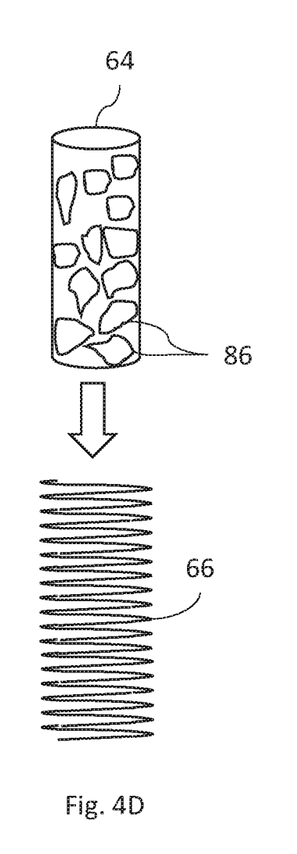

Reference is now made to FIGS. 4A-4D. FIG. 4A is a flowchart 84 including steps in a method of manufacture of the magnetic coil 66 for use in the systems 20a and 20b of FIG. 1A or 1B. FIGS. 4B-4D are schematic views illustrating the method of manufacture described with reference to the flowchart 84 of FIG. 4A.

The method of manufacture includes introducing (block 88) separate powder granules 86 (only some labeled for the sake of simplicity) of a ferrite into the tube 64 as illustrated in FIG. 4B. The tube 64 may be made of any suitable material which can be heat-shrunk, for example, but not limited to, a wide-range of thermoplastics, e.g., polyamide, polyethylene terephthalate (PET), fluorinated ethylene propylene (FEP), or polyvinyl chloride (PVC). While the powder granules 86 are introduced into the tube 64, the plastic tube has an outer diameter which is greater than an inner diameter of the coil 66. For example, if the inner diameter of the coil is 180 microns, the outer diameter of the tube 64 in to which the powder granules 86 are disposed has an outer diameter of 250 microns and an inner diameter of about 180 microns. The outer diameter of the tube 64 shrinks to 180 microns after being heat shrunk as described in more detail below. The preshrunk tube 64 may have any suitable outer diameter in accordance with the inner diameter of the coil 66 and the heat shrink properties of the plastic tube. The preshrunk tube 64 may have any suitable outer diameter, for example, in the range of 150-1200 microns. The powder granules 86 are placed as separate granules in the tube 64 and are not bound together to form a solid mass using heat and/or pressure after being placed in the tube 64. The powder granules 86 may be bound together after being placed in the tube 64 using a binder such as a low viscosity epoxy, which may be wicked in to the tube 64 with capillary action after the tube 64 is shrunk, or before the tube 64 is shrunk and then the tube 64 is shrunk while the epoxy is still liquid as it would not be possible to shrink the tube 74 once the epoxy is cured. The powder granules 86 may have any suitable size which is less than the inner diameter of the tube 64 in to which the powder granules 86 are disposed.

The powder granules 86 may be introduced into the tube 64 using any suitable method. For example, the powder granules 86 may be introduced into the tube 64 with the aid of a funnel which is aligned with the tube opening. The funnel is filled with the powder granules 86 and is vibrated up and down, and/or side-to-side, using any suitable vibration method, such as an ultrasonic method. The funnel may be connected with the tube 64, and vibrated in unison with the tube 64 to facilitate the introduction of the powder granules 86 into the tube 64.

Additionally, or alternatively, one or more magnets (electromagnetics and/or permanent magnets) may be connected to the tube 64 to facilitate introduction of the powder granules 86 into the tube 64. For example, using a magnetic connected to the bottom of the tube 64 and/or a ring-type magnetic connected around the tube 64. The magnet(s) may allow movement (up and down, and/or sideways movement), vibration (up and down, and/or sideways vibration), and/or rotation of the tube 64.

The method incudes heat shrinking (block 90) the tube 64 to have an outer diameter equal to the inner diameter of the coil 66 as illustrated in FIG. 4C. For example, the tube 64 is shrunk from an outer diameter of 250 microns to 180 microns. The inner diameter of the shrunk tube 64 is generally less than 150 microns and typically in the range of 100 to 750 microns. The heat applied in the heat shrinking process is sufficient to shrink the tube 64 but not enough to cause the powder granules 86 to form a solid mass through sintering.

The method then includes disposing the coil 66 around the tube 64, typically by inserting (block 92) tube 64 into coil 66 as illustrated in FIG. 4D.

Figure 5A:
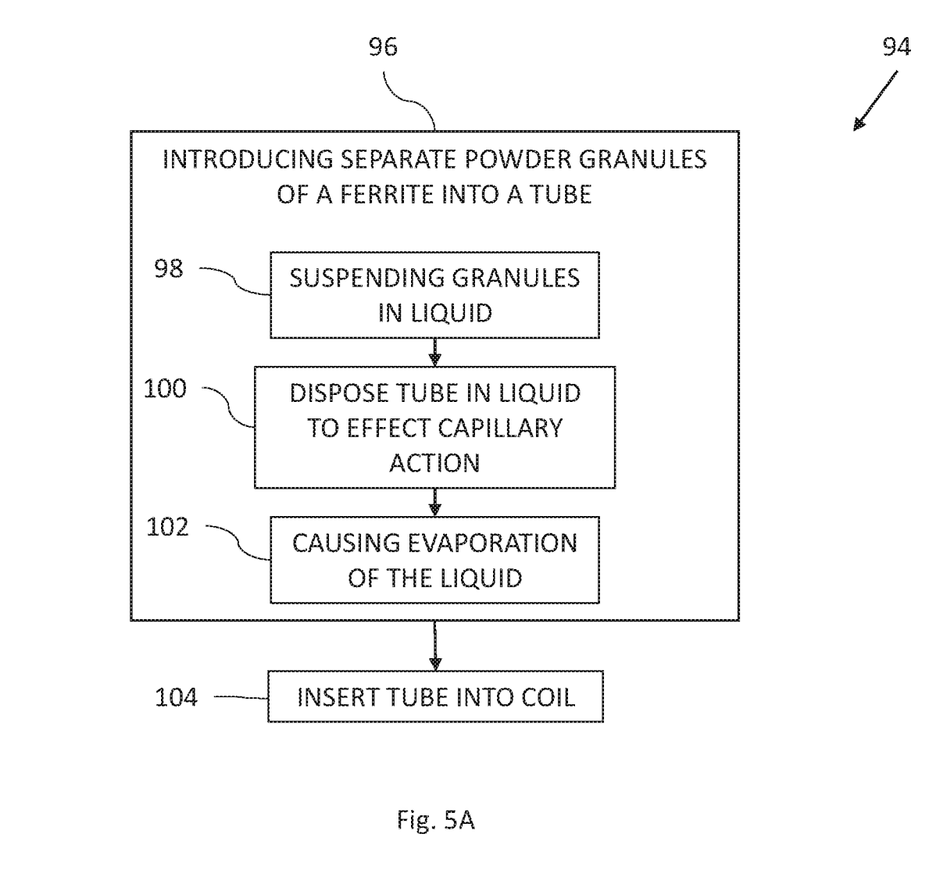
FIG. 5A is a flowchart including steps in an alternative method of manufacture of a magnetic coil for use in the systems of FIG. 1A or 1B.

Reference is now made to FIGS. 5A-E. FIG. 5A is a flowchart 94 including steps in an alternative method of manufacture of the magnetic coil 66 for use in the systems 20a and 20b of FIG. 1A or 1B. FIGS. 5B-5E are schematic views illustrating the alternative method of manufacture described with reference to the flowchart 94 of FIG. 5A.

The method of manufacture includes introducing (block 96) separate powder granules 86 (only some labeled for the sake of simplicity) of a ferrite into the tube 64. The step of block 96 in now described in more detail with reference to sub-steps of blocks 98-102.

Figure 5B:
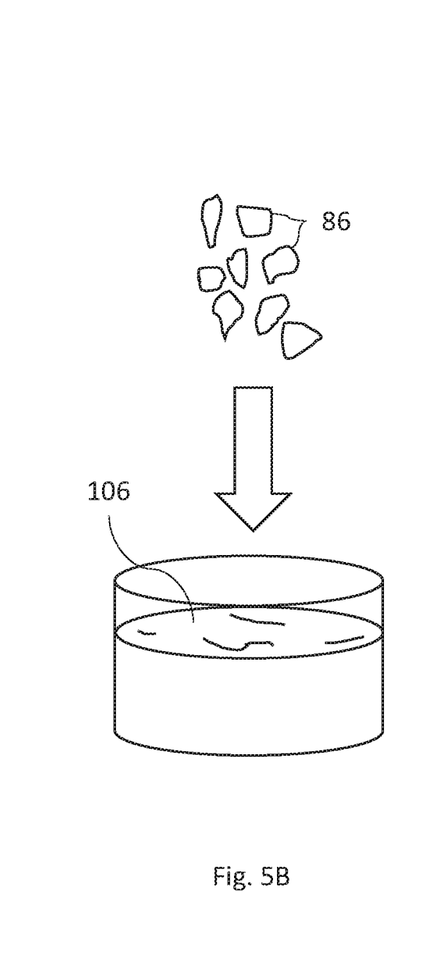
FIGS. 5B-5E are schematic views illustrating the alternative method of manufacture described with reference to the flowchart of FIG. 5A.

The method incudes suspending (block 98) the powder granules 86 in a liquid 106, such as an alcohol, for example, but not limited to, isopropyl alcohol, or any other liquid which has a sufficiently low viscosity and a high enough evaporation rate, as illustrated in FIG. 5B. The suspending may be performed using any suitable method for example, but not limited to, placing the powder granules 86 with the liquid in a container on a vibration table (not shown) or by using any other vibration method, such as using ultrasound. The percentage of powder granules in the suspension, by volume, may be any suitable value, for example, in the range of 30-70%.

Figure 5C:
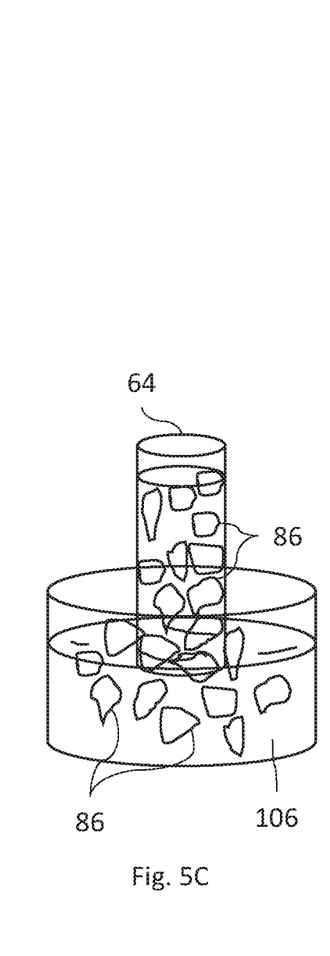

The method incudes disposing (block 100) an end of the tube 64 in the liquid 106 so that capillary action draws some of the liquid 106 with the powder granules 86 into the tube 64 as illustrated in FIG. 5C. The tube 64 has an outer diameter less than the inner diameter of the coil 66, for example, in the range of 150 to 800 microns. The inner diameter of the tube 64 is generally less than 150 microns and typically in the range of 100 to 750 microns. The tube 64 may be made of any suitable material, for example, but not limited to, plastic, an engineered ceramic, a carbon material, or a non-ferromagnetic metal.

Figure 5D:
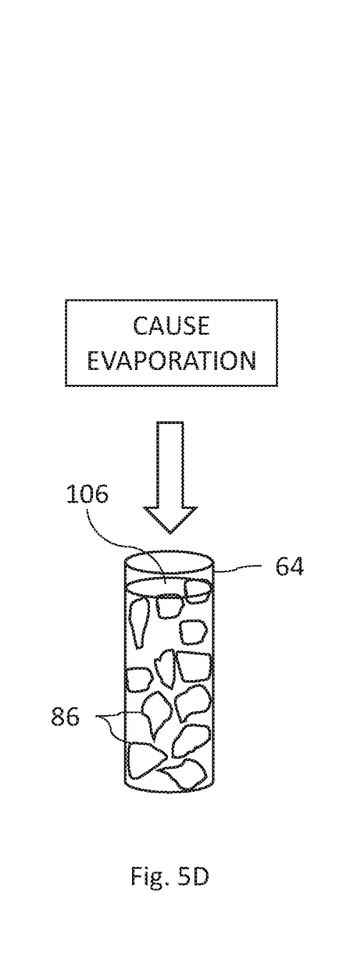

The method incudes causing evaporation (block 102) of the liquid 106 from the tube 64 as illustrated in FIG. 5D. The evaporation may be caused using any suitable method such as using heat and/or blowing air over the tube 64. After the evaporation, a binder such as a low viscosity epoxy may be wicked into the tube 68 with capillary action to bind the powder granules 86 together.

Figure 5E:
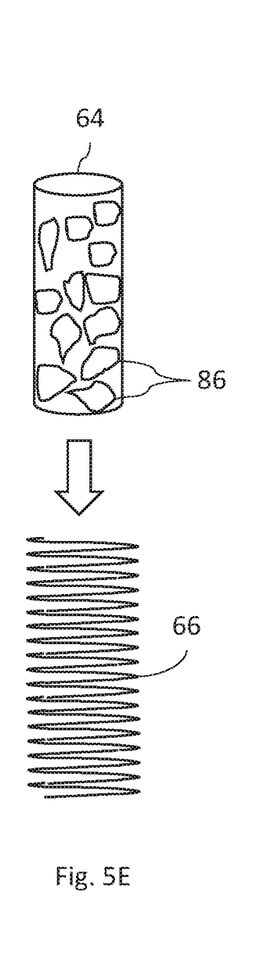

The method incudes disposing the coil 66 around the tube 64, typically by inserting (block 104) tube 64 into coil 66 as illustrated in FIG. 5E.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A probe apparatus, comprising:
   a shaft having a distal end;
   a tube comprising a thermoplastic material, the tube being fixed to the distal end of the shaft and having an inner diameter and an outer diameter that have been reduced through a heat shrink process such that the inner diameter is less than 150 microns;
   unbound powder granules of ferrite contained within the inner diameter of the tube;
   a coil disposed around the outer diameter of the tube; and
   electrical wires connected to the coil so as to read out a signal generated across the coil due to an externally-applied magnetic field, wherein the electrical wires comprise twisted pair conductors.

2. The apparatus according to claim 1, further comprising a guidewire including:
   a solid rod core wire comprising a distal end and a surface channel for accepting the electrical wires therein;
   a shapeable elongated member, connected to the distal end of the core wire, and configured to retain a shape after being deformed; and
   a resilient elongated member disposed around the shapeable elongated member, wherein the tube is disposed distally to the resilient elongated member and the shapeable elongated member.

3. The apparatus according to claim 2, wherein the surface channel spirals around the core wire away from the distal end of the core wire.

4. The apparatus according to claim 2, wherein the shapeable elongated member includes a flat wire helical spring.

5. The apparatus according to claim 2, wherein the resilient elongated member comprises an outside surface including a plurality of cut grooves disposed around the outside surface.

6. The apparatus according to claim 2, wherein the guidewire comprises a shrink sleeve disposed over the core wire retaining the electrical wires in the surface channel.

7. The apparatus according to claim 2, wherein the electrical wires are disposed through a center of the shapeable elongated member.

8. The apparatus according to claim 1, wherein the thermoplastic includes polyimide, polyethylene terephthalate, fluorinated ethylene propylene, or polyvinyl chloride.

9. The apparatus of according to claim 1, wherein the outer diameter of the tube is equal to or less than an inner diameter of the coil.

10. The apparatus according to claim 1, wherein the outer diameter of the tube is equal to an inner diameter of the coil.

11. A position tracking system, comprising:
    a probe configured to be inserted into a body part of a living subject, and comprising:
      a shaft having a distal end;
      a tube comprising a thermoplastic material, the tube being fixed to the distal end of the shaft and having an inner diameter and an outer diameter that have been reduced through a heat shrink process such that the inner diameter is less than 150 microns;
      unbound powder granules of ferrite contained within the inner diameter of the tube;
      a coil disposed around the outer diameter of the tube; and
      electrical wires connected to the coil so as to read out a signal generated across the coil due to an applied magnetic field, wherein the electrical wires comprise twisted pair conductors;
    a location pad having at least one magnetic field radiator configured to transmit alternating magnetic fields into a region where the body part is located; and
    processing circuitry coupled to the electrical wires, and configured to: receive the signal from the coil; and compute a position and orientation of the distal end responsively to the received signal.

12. The system according to claim 11, wherein the probe includes a guidewire comprising:
    a solid rod core wire comprising a distal end and a surface channel for accepting the electrical wires therein;
    a shapeable elongated member, connected to the distal end of the core wire, and configured to retain a shape after being deformed; and a resilient elongated member disposed around the shapeable elongated member, wherein the tube is disposed distally to the resilient elongated member and the shapeable elongated member.

13. The system according to claim 12, wherein the electrical wires are disposed through a center of the shapeable elongated member.

14. The system according to claim 11, wherein the thermoplastic includes polyimide, polyethylene terephthalate, fluorinated ethylene propylene, or polyvinyl chloride.

15. The system according to claim 11, wherein the outer diameter of the tube is equal to or less than an inner diameter of the coil.

16. The system according to claim 11, wherein the outer diameter of the tube is equal to an inner diameter of the coil.

* * * * *